(12) United States Patent
Kuo

(10) Patent No.: US 8,235,715 B2
(45) Date of Patent: Aug. 7, 2012

(54) UV AND CHEMICAL CURE BLOCKING DENTAL TEMPLATE

(75) Inventor: Eric Kuo, Foster City, CA (US)

(73) Assignee: Align Technology, Inc., San Jose, CA (US)

(*) Notice: Subject to any disclaimer, the term of this patent is extended or adjusted under 35 U.S.C. 154(b) by 420 days.

(21) Appl. No.: 12/338,336

(22) Filed: Dec. 18, 2008

(65) Prior Publication Data

US 2010/0159413 A1 Jun. 24, 2010

(51) Int. Cl.
*A61C 3/00* (2006.01)

(52) U.S. Cl. .......................................................... 433/24

(58) Field of Classification Search .................... 433/18, 433/24
See application file for complete search history.

(56) References Cited

U.S. PATENT DOCUMENTS

| | | | | |
|---|---|---|---|---|
| 3,949,477 A | * | 4/1976 | Cohen et al. | 433/9 |
| 5,971,754 A | * | 10/1999 | Sondhi et al. | 433/24 |
| 6,123,544 A | * | 9/2000 | Cleary | 433/24 |
| 6,905,337 B1 | * | 6/2005 | Sachdeva | 433/229 |
| 6,918,761 B2 | * | 7/2005 | Sachdeva et al. | 433/24 |
| 7,252,509 B2 | * | 8/2007 | Sachdeva | 433/229 |
| 7,347,688 B2 | * | 3/2008 | Kopelman et al. | 433/24 |
| 7,387,511 B2 | * | 6/2008 | Marshall | 433/3 |
| 7,600,999 B2 | * | 10/2009 | Knopp | 433/24 |
| 7,613,527 B2 | * | 11/2009 | Raby et al. | 700/17 |
| 2004/0214131 A1 | * | 10/2004 | Fischer et al. | 433/29 |

* cited by examiner

*Primary Examiner* — Ralph Lewis

(57) ABSTRACT

A dental template formed of an ultraviolet light-blocking or chemical cure inhibition material configured to restrict the curing of excess adhesive flash during the bonding of orthodontic devices to teeth. The dental template is configured to be positioned over a patient's teeth to guide placement of brackets on the teeth. The brackets are secured to the teeth using adhesive, which is cured by exposure to ultraviolet light or chemically cured. The dental template at least partially blocks ultraviolet light or restricts the chemical cure process from fully curing the adhesive underneath the template so that any exposed adhesive "flash" underneath the template can be easily cleaned after the template is removed from the teeth. The adhesive securing the brackets to the teeth can be fully cured after the "flash" is cleaned.

25 Claims, 4 Drawing Sheets

20 — Place the Template on the Patient's Teeth

22 — Mount the Orthodontic Object on the Tooth Using Template as Guide

24 — Bond the Orthodontic Object to the Tooth

UV AND CHEMICAL CURE BLOCKING DENTAL TEMPLATE

BACKGROUND

The present invention relates generally to the field of orthodontics, and more particularly to an apparatus for bonding an orthodontic bracket to a tooth and a method for making the same.

The fundamental objectives in orthodontics are to move a patient's teeth to a position where the mechanical function of the dentition is optimized and to improve the aesthetic appearance of the patient's teeth. The traditional method that orthodontists use is to attach brackets and wires onto the patient's dentition. Once mounted on the teeth, the wires exert continual light forces through the brackets on the teeth. These forces initiate the body's biological bone remodeling response and the teeth gradually progress toward their desired final positions. During the treatment period, the treatment professional reactively adjusts the wires and bands to provide a new force and move the teeth generally toward their desired or final destination.

Orthodontic brackets are often bonded directly to the patient's teeth. Typically, a small quantity of adhesive is placed on the base of each bracket and the bracket is then placed on a selected tooth while the patient is in the dental chair. Before the adhesive is set, the bracket is maneuvered to a general location on the tooth. Once the adhesive has hardened or cured, the bracket is bonded to the tooth with sufficient strength to withstand subsequent orthodontic forces as treatment progresses. Bonding templates can be used by an orthodontist for positioning the bracket at the desired location on the tooth. However, one shortcoming with this technique is the difficulty in cleaning adhesive "flash" that typically forms on the teeth around the edges of the brackets under the template. The adhesive flash under the template is not easily accessible while the template is on the teeth prior to curing of the adhesive. As cleaning of adhesive flash after it has hardened or cured is difficult, the amount of time needed to carry out the direct bonding procedure is thus increased.

One way to overcome some of the limitations of direct bracket placement is with indirect bonding. Typically, a routine impression of each of the patient's upper and lower dental arches is taken and either sent to a lab or used in the office to create a replica plaster model of each impression after the patient has left the office. Brackets are bonded to the sealed plaster models using a temporary adhesive. A transfer tray is then made by placing matrix material over both the model and brackets. The matrix material then assumes a configuration that matches the shape of the replica teeth of the plaster model with the brackets in the desired position. The matrix material then polymerizes and hardens to form a tray. The temporary adhesive is removed, and permanent adhesive is placed on the base of each bracket in the tray, which is then placed over matching portions of the patient's dental arches. Since the configuration of the interior surface of the tray closely matches the respective portions of the patient's dental arches, each bracket location is transferred onto the patient's teeth at precisely the same location that corresponds to the previous location of the same bracket on the plaster model. The adhesive is hardened or cured and the matrix removed, leaving the brackets in the desired positions on the teeth. The tray may be provided with bracket placement "fingers," which allow access to tooth surfaces around the brackets, facilitating cleanup of any adhesive flash that may form on the teeth. The indirect bonding method, however, is labor intensive and the brackets may become dislodged during the removal of the matrix from the dental arches. Thus, a direct bonding template that would allow cleanup of adhesive flash prior to curing would be desirable.

SUMMARY

In accordance with one embodiment, a method is provided for fabricating a dental template configured to position an object on teeth of a patient. A digital model of the patient's teeth is created. A template model comprising teeth based on the digital model is created. The dental template is fabricated using the template model. The dental template includes an ultraviolet light-blocking material configured to at least partially block ultraviolet light.

DESCRIPTION

Embodiments of a dental template are disclosed to support positioning an object on a patient's tooth oriented in such a way that all objects as a whole are lined up to a user defined ideal arrangement and the template also allows cleanup of all adhesive flash prior to curing. Also, a method is disclosed for fabricating the template. The method includes digitizing the patient's teeth; adding virtual objects to predetermined locations on the digitized teeth; and fabricating the dental template to locate the object on the patient's teeth. The dental template is designed to locate each object at a predetermined inclination or a predetermined angulation on the patient's tooth and for preventing complete curing of adhesive flash, which results from adhering the objects to the teeth. The template can be used for etching or for positioning brackets on teeth. The skilled artisan will understand that the elements of the template and/or concepts of the fabrication methods described herein can be mixed and matched. For example, a template may be created using some steps from one method and other steps from one or more other methods.

The template is formed of a polymeric shell having a cavity shaped to fit over a patient's teeth and has openings that allow brackets, which can be standardized, to be accurately positioned on teeth regardless of tooth surface variations from the norm for which the bracket base is designed. The treatment can be done virtually and the placement of the brackets can be done using a template device that is a removable guide. This device allows precise placement of the bracket and enable brackets placement onto specific teeth independent of overall arch geometry. The template makes it easier for a less well-trained or an untrained person to bond a bracket. The system minimizes variations in the perception of distance and angles. The template allows precise control of the placement of the bracket. Since bracket placement is one of the critical variables to successful treatment, the template improves treatment precision from patient to patient and from tooth to tooth.

Figure 1:
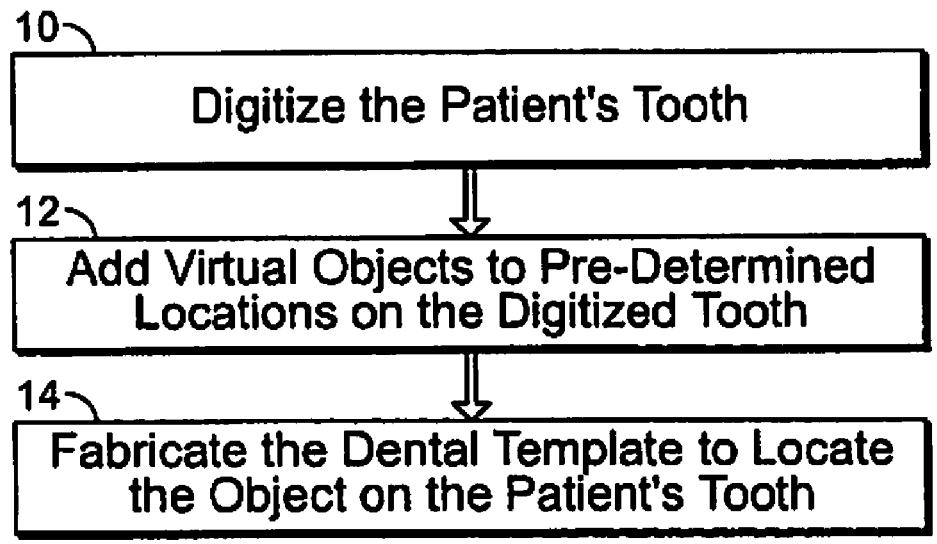
FIG. 1 shows an exemplary process for fabricating a dental template for positioning an object on a patient's tooth.

FIG. 1 shows an exemplary method or process of fabricating a dental template for positioning an object on a patient's tooth. First, the process digitizes the patient's tooth (10). Next, virtual objects are added to pre-determined locations on the digitized tooth (12). Finally, the process fabricates the dental template to locate the object on the patient's tooth (14). One detailed implementation of the method of FIG. 1 is described with reference to FIG. 3A below.

Figure 2A:
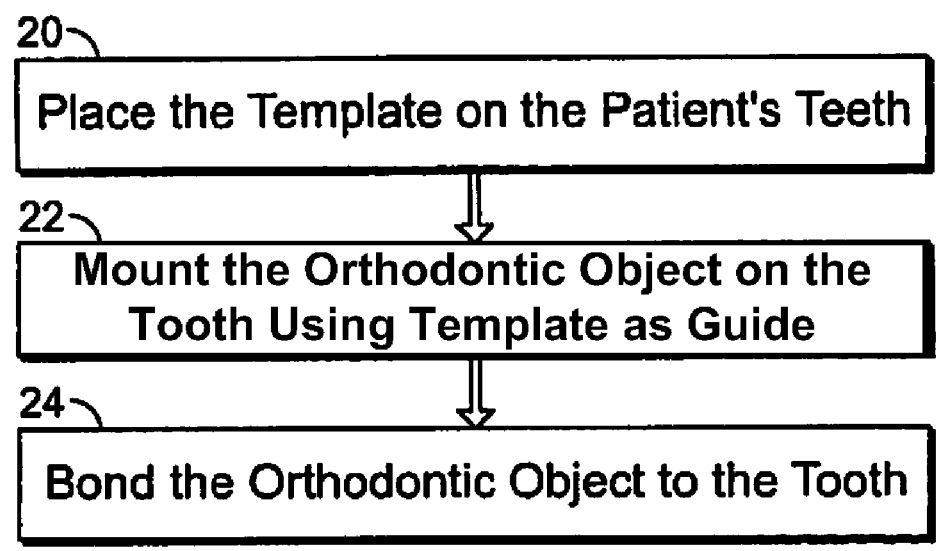
FIG. 2A shows an exemplary process for placing an orthodontic object on a patient's tooth.

FIG. 2A shows an exemplary direct bonding method or process for placing an orthodontic object on a patient's tooth. The process uses a template, such as the one fabricated in the process of FIG. 1. The process includes placing the template on the patient's teeth (20); mounting the orthodontic object on the tooth using the template as a guide (22); and bonding the orthodontic object to the tooth (24). In the bonding operation, chemical curing or light curing adhesives can be used. In chemical curing, separately supplied curing components are mixed together and a small quantity of the mixture is placed on the back of the bracket prior to placing the bracket on the tooth. Light-curable adhesives include a photo-initiator that initiates the curing reaction once the adhesive is exposed to a sufficient amount of light. A common method of using light-curable adhesives for direct bonding includes the steps of placing a small quantity of the adhesive on the base of the bracket and then placing the bracket on the patient's tooth. The practitioner then shifts the bracket on the tooth as may be needed. Once the bracket is in its intended location, light from a dental curing unit is directed toward the adhesive for a time period sufficient to satisfactorily cure the adhesive. In another embodiment, a chemical cure adhesive is used to secure the bracket and the adhesive is chemically cured.

Figure 2B:
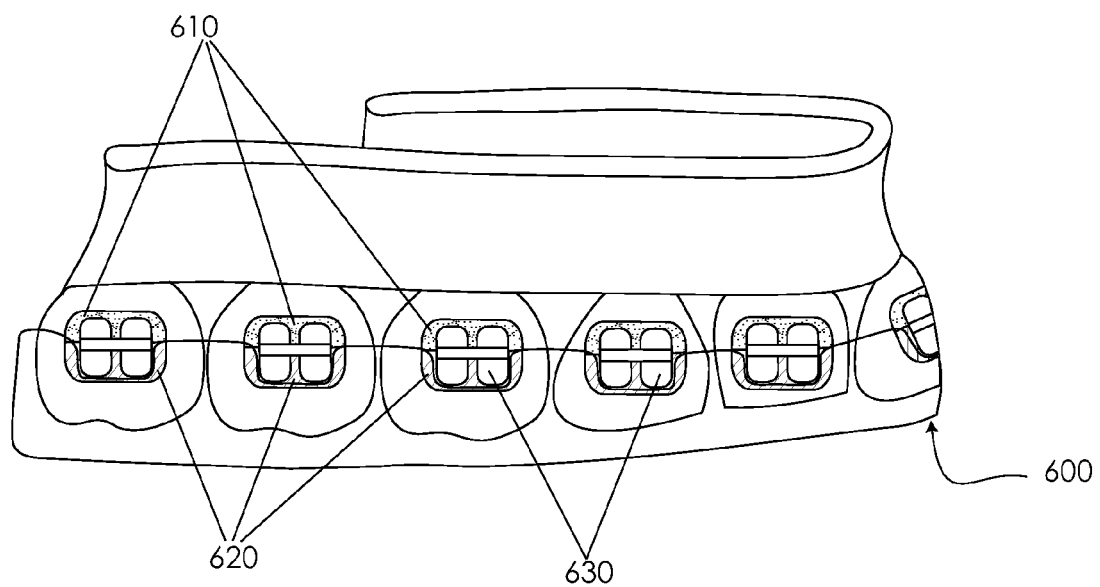
FIG. 2B shows an embodiment of a thermoformed direct bond dental template.

The skilled artisan will appreciate that when a direct-bonding thermoformed or chemical- or light-set formed template is positioned on a patient's teeth, adhesive "flash" can form on the teeth around the edges of the brackets and cannot be easily cleaned. FIG. 2B shows an embodiment of a thermoformed direct bonding template 600. Direct bonding templates are typically used to position brackets on a patient's teeth. As shown in FIG. 2B, adhesive "flash" 610, 620 forms when the template 600 and brackets 630 are positioned on the teeth. Those of skill in the art will appreciate that the portion of the adhesive "flash" 610 that forms around the edges of the brackets 630 between the template 600 and the teeth is more difficult to clean than the portion of the adhesive "flash" 620 that forms on the teeth but not underneath the template 600, as shown in FIG. 2B. The "flash" 620 can also be a stain and plaque trap if not removed. The portion of the adhesive "flash" 620 that is not underneath the template 600 can be cleaned while the template 600 is positioned on the teeth before the adhesive is cured. Because the adhesive is cured prior to removing the template 600 from the teeth using, the adhesive "flash" 620 underneath the template 600 is typically also cured, and therefore difficult to remove/clean, after the template 600 is removed from the teeth when the adhesive "flash" 620 is hardened.

According to an embodiment, the object or bracket is adhered to the tooth using an ultraviolet light-cured adhesive. The adhesive is cured using ultraviolet (UV) light. Thus, in this embodiment, the template 600 is formed of a UV blocking material that at least partially blocks the UV light during the curing process. With the template 600 formed of UV blocking material, during the curing process, the portion of the adhesive "flash" 620 underneath the template 600 is only partially or entirely un-cured, and therefore easier to clean after the template 600 is removed from the teeth. After the adhesive "flash" 610, 620 is removed (after the template 600 is removed), the adhesive securing the brackets 630 to the patient's teeth can be fully cured with minimal flash. Suitable UV blocking materials include, but are not limited to, UV absorbing agents (e.g., para-amino Benzoic acid), UV absorbing dyes and reflective coatings (e.g., orange UV blocking plastics) and opaquing agents introduced into the plastic composition to reduce/eliminate transmission of the wavelength of the photoinitiator. Furthermore, the use of a colored UV blocking material for the template 600 also makes the seated position of brackets 630 in the template 600 easier to verify because the different color of the template 600 marks the bracket-interfacing portions of the template 600, thus marking a border (which may be needed on a transparent or white template) unnecessary.

According to another embodiment in which a chemical-cure adhesive is used, the template 600 can contain chemicals that chemically react with the adhesive to block or retard the reaction of the adhesive components to prevent or slow curing of the portion of the adhesive "flash" 620 underneath the template 600. For example, eugenol is a common dental material, which is also a free-radical inhibitor, that inhibits the free radical-initiated polymerization of chemical cure dental composites. Thus, the skilled artisan will readily appreciate that a free radical inhibitor embedded into the template 600 material would be an effective chemical cure blocker to enable easier cleaning of the adhesive "flash" 620.

As shown in FIG. 2B, the template 600 has openings for guiding the placement of brackets 630 on the teeth. According to an embodiment, the edges of a template 600 formed of a colored UV or chemical cure blocking material can be a guide for positioning the bracket 630 on a patient's tooth. In this embodiment, the colored edge of the template 600 can be easily seen against a white tooth and indicates the template-bracket interface. The template 600 may also be used as a guide for enamel etching or adhesive placement. The etching template directs the user to predetermined locations on the teeth surface that need to be bonded. The etching template can be either a windowed template or a concave surfaced template where bonding gel is loaded or pre-loaded into the concavity.

Figure 3A:
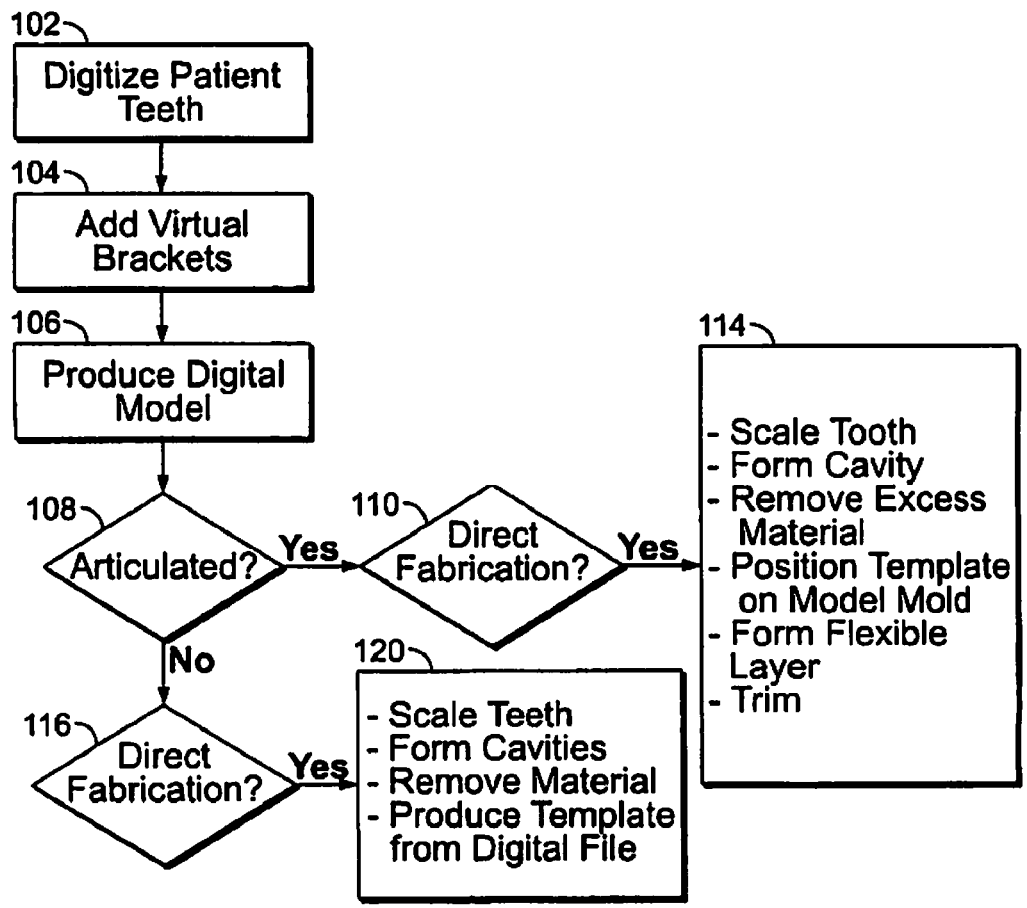
FIG. 3A illustrates an exemplary process for fabricating the dental template

FIG. 3A illustrates an exemplary process for fabricating the dental template. First, a digital model of a patient's teeth is obtained (102). The digital model can be obtained in a variety of ways. For example, the patient's teeth, models thereof or impressions may be scanned or imaged using well-known technology, such as two or three dimensional X-rays, computer-aided tomographic images or data sets, magnetic resonance images, etc. There are a variety of range acquisition systems, generally categorized by whether the process of acquisition requires contact with the three dimensional object (e.g., tooth) to be imaged. A contact-type range acquisition system uses a probe having multiple degrees of translational and/or rotational freedom. By recording the physical displacement of the probe as it is drawn across the sample surface of the object, a computer-readable representation of the sample object is made. A non-contact type range acquisition device can be either a reflective-type or transmissive-type system. There are a variety of reflective systems in use. Some of these reflective systems use non-optical incident energy sources, such as microwave radar or sonar. Others use optical energy. The non-contact type systems working by reflected optical energy further contain special instrumentation configured to permit certain measuring techniques to be performed (e.g., imaging radar, triangulation, and interferometry).

Next, virtual brackets are selected and added (104) to the digital model of the patient's teeth. The virtual brackets are three-dimensional (3D) virtual models of physical brackets. The 3D model may be a computer aided design (CAD) model or may be scanned using scanners, as described above. The virtual brackets may be positioned on a digitized tooth using a computer or workstation having a suitable graphical user interface (GUI) and software appropriate for viewing and modifying the images. The above-described component identification and component manipulation software is designed to operate at sophistication commensurate with the operator's training level. For example, the component manipulation software can assist a computer operator, lacking orthodontic training, by providing feedback regarding permissible and forbidden manipulations on the teeth. On the other hand, an orthodontist, having greater skill in intra-oral physiology and teeth-moving dynamics, can simply use the component identification and manipulation software as a tool and disable or otherwise ignore the device.

While the methods described herein may rely on computer manipulation of digital data, the dental template or appliance may be produced by non-computer-aided techniques. For example, plaster casts, obtained as described above, may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare the template using pressure and vacuum molding techniques. While such manual creation of the appliance systems will generally be less preferred, appliance systems so produced will come within the scope of the present invention.

According to an embodiment, using the CAD workstation, a combined digital model of the virtual brackets and the teeth can be produced (106). In one implementation, one of two of the following template embodiments can be selected: Direct-Articulated and Direct-Unified, as discussed in more detail with reference to FIG. 3B. The invention described could also apply to indirect bonding templates, since the problem of excessive adhesive flash is also a problem encountered with indirect bonding placement of brackets. With the direct bond template, a portion of the flash can be removed through visual inspection prior to adhesive curing, whereas with most indirect bonding systems, any excess adhesive cannot be removed prior to curing.

Once the template has been fabricated, according to one embodiment, the system sets the template over the model of the patient's dental arches or otherwise positions the template in the approximate locations of their respective teeth. A thermoformed cast, or otherwise formed layer of flexible material, is deposited on the bodies of the templates and makes relatively durable contact with the bodies of the templates. This method may be performed either in a factory or in an orthodontist's office.

The system can produce both the template bodies and the inter-tooth position(s) at the same time and subsequently alters the stiffness of the various parts. One way of achieving this would be to produce the entire arch with a 3D printer, mask the tooth bodies from the inter-tooth portions, and invest the tooth bodies with a rigidifying agent and the inter-tooth portions with an agent to create flexibility.

As shown in FIG. 3A, from 110, if a directly formed template is produced, the process proceeds to 114, where each tooth is scaled; a cavity is then formed to enclose the tooth when the dental template or appliance is inserted over the patient's teeth. Next, excess material or unnecessary structures (e.g., anatomies of certain teeth, occlusal portions, gingival portions) are removed from the digital model. The digital model is produced as a physical model. A flexible, pliable layer is formed and the resulting combination is trimmed to allow proper fit and function.

From 108, if a template of a whole arch (not articulated) is to be produced, the process proceeds to 116. In the case of a directly formed whole arch template, the process proceeds from 116 to 120 where the entire arch is scaled; cavities are then formed to enclose the arch when the dental template or appliance is inserted over the patient's teeth. Next, excess material or unnecessary structures (e.g., certain teeth, occlusal portions, gingival portions) are removed from the digital model. The digital model is produced as a physical model. A flexible, pliable layer is formed and the resulting combination is trimmed to allow proper fit and function. According to an embodiment, this flexible, pliable thermoformed layer is formed of a UV-blocking material. Materials used in thermoforming can include, but are not limited to, polycarbonates, polyurethanes, polyacrylics, polyesters and polystyrenes. The template may also be a multi-layer thermoformed plastic construction wherein one layer is the blocking layer and the other layer is a base layer.

Figure 3B:
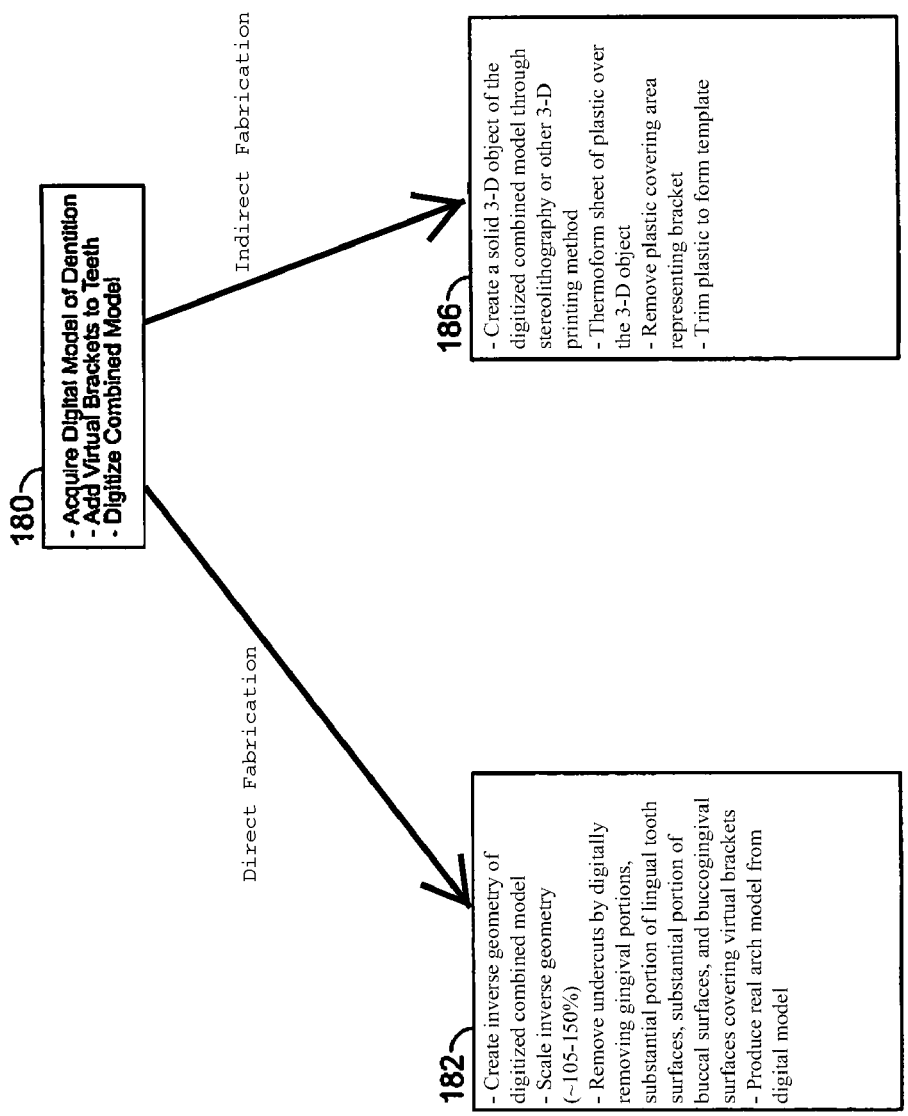
FIG. 3B shows a process for providing two possible direct bond templates.

FIG. 3B shows a process with two options for providing two possible direct bonding templates. One option is a direct fabrication of a template, and the other option is an indirect fabrication of a template. In both techniques, the process acquires a digital model of dentition, adds virtual brackets to the teeth, and creates a combined model (180) including the dentition and the virtual brackets. Next, one of two template options can be selected.

The first option is the direct fabrication method. In this method, the process creates an inverse geometry of the digital model of the teeth containing the digital brackets from a solid digital object. Any undercuts are removed, thereby enabling this digital object to be positioned over the actual teeth without interference. The inverse geometry may be scaled from 105-150% prior to creating the solid digital object in order to facilitate seating of the final template. To remove the undercuts, gingival portions, substantial portion of lingual tooth surfaces, substantial portion of the buccal surfaces, and buccogingival surfaces covering virtual brackets are digitally removed to produce a real arch model from the digital model (182).

The second option is the indirect fabrication method. In this method, the process creates a digital representation of the teeth with virtual brackets placed in the desired position. A physical 3-D object (e.g., a mold) of the digital model of the teeth and brackets is created through stereolithography or other 3-D printing (e.g., Fused Deposition Modeling). A sheet of plastic is thermoformed over the 3-D object and the plastic covering the area representing the bracket is removed. The thermoformed plastic is trimmed in such a way that the remaining template can sit atop the actual teeth, with the cut out windows enabling the placement of the actual brackets in the exact position that was represented by the digital brackets in the 3-D print (186). The physical 3-D object can be fabricated using rapid prototyping methods.

In one embodiment, the template 600 is made from a thick material (for example, at least 0.03 inch) to provide the user with more guidance in the depth direction. The template 220 material is preferably about 0.015-0.1 inch, and more preferably about 0.03-0.06 inch thick. Furthermore, the thick template allows easier aligning of the bracket to the tooth as a result of the edge created in the material around the footprint. The template 600 may be made from materials that contain physical property switches for ease of removal. These switches might include temperature responsive, pH responsive, moisture responsive, or a multi-layer system wherein the layers have varying physical properties. More information on the fabrication of a dental template or appliance is disclosed in the following: U.S. patent application Ser. No. 10/794,324, entitled "Systems and Methods for Fabricating A Dental Template With a 3-D Object Placement," filed Mar. 4, 2004; and U.S. Pat. No. 7,056,115, entitled "Systems and Methods for Fabricating a Dental Template," filed Jun. 17, 2004. The entire disclosures of each of the foregoing patents and patent applications are hereby incorporated herein by reference.

Various alternatives, modifications, and equivalents may be used in lieu of the above components. Additionally, the techniques described herein may be implemented in hardware or software, or in a combination of the two. The techniques may be implemented in computer programs executing on programmable computers that each includes a processor, a storage medium readable by the processor (including volatile and nonvolatile memory and/or storage elements), and suitable input and output devices. Each program can be implemented in a high level procedural or object-oriented programming language to operate in conjunction with a computer system. However, the programs can be implemented in assembly or machine language, if desired. The language may also be a compiled or interpreted language. Each such computer program can be stored on a storage medium or device (e.g., CD-ROM, hard disk, magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium causes a computer to operate in a specific and predefined manner. Further, while the invention has been shown and described with reference to certain embodiments thereof, those skilled in the art will understand that the above and other changes in form and detail may be made without departing from the spirit and scope of the following claims.

What is claimed is:

1. A method of fabricating a dental template configured to position an object on teeth of a patient, comprising:
   creating a digital model of the teeth of the patient;
   creating a template model comprising teeth based on the digital model; and
   fabricating the dental template using the template model, the dental template comprising an ultraviolet light-blocking material comprising eugenol and being configured to at least partially block ultraviolet light during a curing process of adhesive material and to react with the adhesive material that adheres the object to the teeth such that a portion of adhesive flash positioned underneath the dental template is either partially or entirely un-cured.

2. The method of claim 1, wherein the ultraviolet light-blocking material is selected from the group consisting of an opaquing agent, a UV absorbing dye, a UV absorbing reflective coating, and a UV absorbing agent.

3. The method of claim 1, wherein fabricating the dental template comprises thermoforming the dental template.

4. The method of claim 1, wherein the template model is created using a rapid prototyping technology.

5. The method of claim 4, wherein the rapid prototyping technology is fused deposition modeling.

6. The method of claim 1, wherein the ultraviolet light-blocking material is a colored material.

7. The method of claim 1, further comprising positioning the object on the template model.

8. A dental template for positioning an object on at least one tooth of a patient, the dental template comprising:
   a polymeric shell having a cavity shaped to fit over the at least one tooth of the patient;
   an opening within the polymeric shell that allows the object to be positioned on the at least one tooth; and
   an ultraviolet light-blocking material configured to react with adhesive material and at least partially block ultraviolet light during a curing process of adhesive material that adheres the object to the at least one tooth such that a portion of adhesive flash positioned underneath the dental template is either partially or entirely un-cured, wherein the ultraviolet light-blocking material comprises eugenol.

9. The dental template of claim 8, wherein the ultraviolet light-blocking material is selected from the group consisting of an opaquing agent, a UV absorbing dye, a UV absorbing reflective coating, and a UV absorbing agent.

10. The dental template of claim 8, wherein the ultraviolet light-blocking material is thermoformed.

11. The dental template of claim 8, wherein the ultraviolet-light blocking material is colored.

12. The dental template of claim 8, comprising a plurality of layers, including a layer comprising the ultraviolet light-blocking material and a base layer.

13. A method of securing an object on a patient's tooth, the method comprising:
   fabricating a dental template comprising a cure inhibiting material;
   positioning the object on the patient's tooth using the dental template as a guide;
   attaching the object to the patient's tooth with adhesive material after positioning the object on the patient's tooth; and
   during a curing process, exposing the patient's tooth, the dental template, and the object to either ultraviolet light or a curing chemical after attaching the object to the patient's tooth, wherein the cure inhibiting material is configured to react with the adhesive material to inhibit curing of adhesive material underneath the template during the curing process, such that a portion of adhesive flash that is positioned underneath the dental template is either partially or entirely un-cured, the cure inhibiting material comprising eugenol.

14. The method of claim 13, further comprising removing exposed portions of the adhesive after exposing the patient's tooth, the template, and the object to either the ultraviolet light or the curing chemical.

15. The method of claim 14, further comprising fully curing adhesive between the object and the patient's tooth.

16. The method of claim 14, further comprising removing the dental template from the patient's tooth before removing exposed portions of the adhesive.

17. The method of claim 16, further comprising removing exposed portions of the adhesive before removing the dental template.

18. The method of claim 17, wherein the dental template is created based on a digital model of the patient's tooth.

19. The method of claim 13, wherein the cure inhibiting material is configured to at least partially block exposure of adhesive underneath the template to ultraviolet light.

20. The method of claim 19, wherein the cure inhibiting material comprises a material selected from the group consisting of an opaquing agent, a UV absorbing dye, a UV absorbing reflective coating, and a UV absorbing agent.

21. The method of claim 13, wherein the cure inhibiting material is configured to chemically react with the adhesive.

22. The method of claim 21, wherein the cure inhibiting material comprises eugenol.

23. A dental template for positioning an object on at least one tooth of a patient, the dental template comprising:

a polymeric shell having a cavity shaped to fit over the at least one tooth of the patient;

an opening with the polymeric shell that allows the object to be positioned on the tooth; and a cure blocking material configured to either at least partially block ultraviolet light or chemically react with an adhesive material during a curing process to at least retard curing of the adhesive material adhering the object to the at least one tooth of the patient when exposed to a chemical, such that a portion of adhesive flash positioned underneath the dental template is either partially or entirely un-cured, wherein the cure blocking material is configured to react with an adhesive material to at least retard curing of the adhesive material, the cure blocking material comprising eugenol.

24. The dental template of claim 23, wherein the template is thermoformed.

25. The dental template of claim 23, comprising a plurality of layers, wherein a first layer comprises the cure blocking material and a second layer is a base layer.

* * * * *